United States Patent
Zhu et al.

(10) Patent No.: US 10,837,278 B2
(45) Date of Patent: Nov. 17, 2020

(54) DEVICE AND METHOD FOR EVALUATING GAS-WATER TWO-PHASE FLOW FRACTURE CONDUCTIVITY OF FRACTURED SHALE

(71) Applicant: University of Science and Technology Beijing, Beijing (CN)

(72) Inventors: Weiyao Zhu, Beijing (CN); Ming Yue, Beijing (CN); Dongxu Ma, Beijing (CN); Ziheng Zhou, Beijing (CN); Hongyan Han, Beijing (CN); Zhiyong Song, Beijing (CN); Wenchao Liu, Beijing (CN)

(73) Assignee: UNIVERSITY OF SCIENCE AND TECHNOLOGY BEIJING, Beijing (CN)

( * ) Notice: Subject to any disclaimer, the term of this patent is extended or adjusted under 35 U.S.C. 154(b) by 29 days.

(21) Appl. No.: 16/475,138

(22) PCT Filed: Sep. 6, 2018

(86) PCT No.: PCT/CN2018/104454
§ 371 (c)(1),
(2) Date: Jul. 1, 2019

(87) PCT Pub. No.: WO2019/095800
PCT Pub. Date: May 23, 2019

(65) Prior Publication Data
US 2019/0330980 A1  Oct. 31, 2019

(30) Foreign Application Priority Data
Nov. 14, 2017 (CN) .......................... 2017 1 1120544

(51) Int. Cl.
*E21B 49/00* (2006.01)
*G01N 15/08* (2006.01)
*E21B 43/26* (2006.01)

(52) U.S. Cl.
CPC ....... *E21B 49/003* (2013.01); *G01N 15/0826* (2013.01); *E21B 43/26* (2013.01); *E21B 49/00* (2013.01); *G01N 15/08* (2013.01)

(58) Field of Classification Search
CPC .... G01N 15/08; G01N 15/0826; E21B 49/00; E21B 49/003
See application file for complete search history.

(56) References Cited

U.S. PATENT DOCUMENTS

| | | | | |
|---|---|---|---|---|
| 3,284,281 A | * | 11/1966 | Thomas | .............. E21B 43/2405 166/259 |
| 2010/0004866 A1 | * | 1/2010 | Rabinovich | .............. G01V 3/28 702/7 |

(Continued)

FOREIGN PATENT DOCUMENTS

| CN | 102830214 A | 12/2012 |
|---|---|---|
| CN | 103954544 A | 7/2014 |

(Continued)

*Primary Examiner* — Yong-Suk (Philip) Ro
(74) *Attorney, Agent, or Firm* — Bayramoglu Law Offices LLC (57) ABSTRACT

A device and a method for evaluating a gas-water two-phase flow fracture conductivity of a fractured shale. The device includes a seepage system, an injection system, a data collecting and processing system and a three-axis shale core holder, wherein the seepage system is subjected to two stages including a water injection stage and a gas flooding stage. When using the device, firstly the initial permeability and initial mass of the shale sample are determined; the water influx test is performed by injecting water to the shale sample until flow rate of the water discharged from the shale core is stable, then the water injection is ended. After the (Continued)

drying device is installed, the shale sample is subjected to gas flooding, and the aqueous fracturing fluid discharged by the gas flooding is collected until the flow meter determines that the gas volume is stable, and then the gas flooding is ended.

7 Claims, 4 Drawing Sheets

(56) References Cited

U.S. PATENT DOCUMENTS

| | | | |
|---|---|---|---|
| 2012/0012307 A1* | 1/2012 | Nevin | E21B 43/02 166/244.1 |
| 2014/0034447 A1* | 2/2014 | Mathena | C10G 1/00 196/46 |
| 2015/0284811 A1* | 10/2015 | Knight | E21B 43/00 506/2 |
| 2016/0069170 A1* | 3/2016 | Zhao | E21B 43/243 166/267 |
| 2017/0167964 A1 | 6/2017 | Liu et al. | |
| 2018/0258760 A1* | 9/2018 | Kashikar | E21B 49/00 |

FOREIGN PATENT DOCUMENTS

| | | |
|---|---|---|
| CN | 104359819 A | 2/2015 |
| CN | 106525690 A | 3/2017 |
| CN | 106596380 A | 4/2017 |
| CN | 107764718 A | 3/2018 |
| CN | 207379891 U | 5/2018 |

* cited by examiner

DEVICE AND METHOD FOR EVALUATING GAS-WATER TWO-PHASE FLOW FRACTURE CONDUCTIVITY OF FRACTURED SHALE

CROSS REFERENCE TO THE RELATED APPLICATIONS

This application is the national phase entry of International Application No. PCT/CN2018/104454, filed on Sep. 6, 2018, which is based upon and claims priority to Chinese Patent Application No. 201711120544.1, filed on Nov. 14, 2017, the entire contents of which are incorporated herein by reference.

TECHNICAL FIELD

The present invention relates to the technical field of oil and gas exploitation, and particularly to a device and a method for evaluating a gas-water two-phase flow fracture conductivity of a fractured shale.

BACKGROUND

With the increasing rise in demand for energy, conventional hydrocarbon resources can no longer meet industrial demand. Shale gas, as an unconventional energy source, has become a hotspot in global hydrocarbon exploration and development. Shale reservoirs have the characteristics of ultra-low porosity and ultra-low permeability, and high volume fracturing needs to be performed on the shale reservoirs relying on large-scale horizontal drilling and multi-stage fracturing techniques to achieve a relatively high yield. Only an excellent fracture conductivity of the shale reservoir can ensure the economical shale gas development.

At present, the fracturing of the shale-gas reservoirs at home and abroad shows that the flowback rate of the fracturing fluid is generally less than 30%. A large amount of water is retained in the shale fracture network, and a series of microcosmic physico-chemical reactions occur inside the shale rock interacting with the water, thereby affecting the fracture conductivity of the shale fracture network. The seepage law of the existing shale gas in the micro fracture is mainly a seepage law aiming at gas phase in the shale micro fracture by performing the pulse method, the differential pressure flow method, etc. in the laboratory, or combination with a seepage law of water phase. The existing seepage law is quite different from the actual conditions of the shale gas exploitation, and has not taken the factor that the water influx affects the fracture conductivity of the shale micro fracture into account. Therefore, it is quite essential to study the effect of the water influx on the fracture conductivity of the shale, simulate the hydraulic development process of the shale in the laboratory, explore the seepage law of gas-liquid two phases in the shale fracture through experiments, and evaluate the impact of the water influx on the fracture conductivity of shale micro fracture.

SUMMARY

In view of the technical problem, the present invention provides a device and a method for evaluating a gas-water two-phase flow fracture conductivity of a fractured shale, which characterizes the amount of irreducible water after the fractured shale is fractured, the permeability of gas-water two phases in the fracture, and the damage evaluation of the water influx on the shale fracture conductivity. The present invention provides a theoretical and experimental basis for a study of an influence rule of an aqueous fracturing fluid on the shale micro fracture conductivity and the shale gas exploitation.

The device includes an injection system, a seepage system, a data collecting and processing system, and a three-axis shale core holder. The injection system includes a gas source, a gas inlet pressure regulating valve, a water inlet pressure regulating valve, a constant-speed constant-pressure pump and an aqueous fracturing fluid. The seepage system, subjected to two stages of a water injection stage and a gas flooding stage, includes a first back pressure pump, a back pressure valve, a second back pressure pump and a drying device. The data collecting and processing system includes a strain gauge detector, an analytical balance data module, an analytical balance, and a flow meter. The three-axis shale core holder is provided in a calorstat, the gas source is connected to the three-axis shale core holder through a pipeline, the constant-speed constant-pressure pump is connected to the three-axis shale core holder through a pipeline, and the water inlet pressure regulating valve is provided between the constant-speed constant-pressure pump and the three-axis shale core holder; the three-axis shale core holder is connected to the first back pressure pump, and the first back pressure pump is connected to the strain gauge detector; when the seepage system is in the water injection stage, the three-axis shale core holder is connected to the flow meter, and when the seepage system is in the gas flooding stage, a gas outlet of the three-axis shale core holder is connected to the drying device. The back pressure valve and the second back pressure pump are provided on the pipeline between the three-axis shale core holder and the drying device. The drying device is provided on the analytical balance, the other end of the drying device is connected to the flow meter, and the analytical balance is connected to the analytical balance data module.

Specifically, the three-axis shale core holder is composed of an inner cavity surrounded by a holder model and an outer cavity outside the holder model, the inner cavity is provided with a shale core, and the outer cavity is a confining pressure cavity; the holder model is in a form of a rubber casing; and the holder model is provided with a gas inlet and a gas outlet.

The gas source is a nitrogen bottle.

A value of a confining pressure in the three-axis shale core holder is set to be at least 1 MPa higher than an inlet pressure of the three-axis shale core holder by the seepage system.

In the water injection stage of the seepage system, the aqueous fracturing fluid is injected into the three-axis shale core holder at a constant rate or constant pressure. The aqueous fracturing fluid subjected to a shale core seepage passes through the gas outlet of the three-axis shale core holder, flows into the flow meter through the back pressure valve for a flow measurement of the aqueous fracturing fluid subjected to the shale core seepage.

In the gas flooding phase of the seepage system, the gas source enters the three-axis shale core holder through the gas inlet pressure regulating valve. The aqueous fracturing fluid subjected to the shale core seepage passes through the gas outlet of the three-axis shale core holder, flows into the drying device through the back pressure valve, and then flows into the flow meter. A mass of the water inside the shale core is obtained by the analytical balance data module according to data of the drying device.

A method of using the device for evaluating the gas-water two-phase flow fracture conductivity of the fractured shale includes the following steps:

(1) preparation stage of an experiment:

S11, cutting and processing a test sample of a shale into a cylinder, fracturing the cylinder, drying the test sample of the shale after cutting and processing at 102° C. for 24 hours;

S12, obtaining a cross-sectional area and a length of the test sample of the shale after drying, coating a side of the cylindrical shale core after drying with an epoxy silica gel, and weighting after drying;

S13, setting a temperature of the calorstat to 45° C.; and

S14, putting the test sample into the three-axis shale core holder; setting the back pressure valve, adding a confining pressure to the first back pressure pump, after the confining pressure is constant for 12 hours, starting the experiment, and measuring an initial permeability by a gas injection seepage system;

(2) water injection stage:

closing the gas inlet pressure regulating valve, setting the constant-speed constant-pressure pump as a constant pressure injection, setting an injection pressure according to a specific condition of the shale core, opening the water inlet pressure regulating valve, making the aqueous fracturing fluid subjected to the shale core seepage pass through the gas outlet of the three-axis shale core holder, and flow into the flow meter through the back pressure valve for a flow measurement of the aqueous fracturing fluid subjected to the shale core seepage by the flow meter; when the flow rate of the outlet water remains unchanged within 24 hours, ending the water injection, recording the flow rate in this process, obtaining a permeability by Darcy's law, and plotting a curve of change in the permeability measured with water over time; meanwhile, collecting a discharged liquid from the flow meter, and subtracting a discharging amount of the aqueous fracturing fluid from an injection amount of the aqueous fracturing fluid to obtain a retention amount of the water in the shale core;

(3) gas flooding stage:

closing the water inlet pressure regulating valve, installing the drying device, the analytical balance, and the analytical balance data module; setting an inlet pressure of the gas source according to the specific condition of the shale core, opening and adjusting the gas inlet pressure regulating valve, starting the injection of gas into the three-axis shale core holder, and making the aqueous fracturing fluid subjected to the shale core seepage pass through the gas outlet of the three-axis shale core holder, and flow into the flow meter after flowing into the drying device through the back pressure valve; when the flow meter detects that the flow rate remains unchanged within 24 hours, ending the gas injection, recording the flow rate in this process, obtaining a permeability by Darcy's law, and plotting a curve of change in the permeability measured with gas over time; and (4) data processing S41, performing the data processing after closing the experimental device, and plotting the curve of the change in the permeability measured with water over time and the curve of change in the permeability measured with gas over time to study a permeability change;

S42, using the analytical balance data module to obtain a quality of the water discharged from the shale core by the gas flooding in the gas flooding stage, subtracting the mass of the water discharged by the gas flooding from the retention amount of the water in the shale core to obtain an amount of irreducible water in the shale fracture after the intrusion of the aqueous fracturing fluid;

S43, after the gas flooding phase is stable, obtaining the permeability K, an initial permeability is $K_0$, and then a permeability damage rate $f$ can be obtained by the following formula:

$$f = \frac{K - K_0}{K} \times 100\%.$$

The advantages of the above technical solution of the present invention are as follows:

In the above technical solution, the device and method can accurately determine the seepage law of the shale gas in the micro fracture, and the operation is simple, which provides a theoretical and experimental basis for a study of an influence rule of an aqueous fracturing fluid on the shale micro fracture conductivity and the shale gas exploitation.

In the figures: 1—gas source; 2—gas inlet pressure regulating valve; 3—water inlet pressure regulating valve; 4—constant-speed constant-pressure pump; 5—aqueous fracturing fluid; 6—calorstat; 7—three-axis shale core holder; 8—first back pressure pump; 9—strain gauge detector; 10—back pressure valve; 11—second back pressure pump; 12—drying device; 13—analytical balance data module; 14—analytical balance; and 15—flow meter.

DETAILED DESCRIPTION OF THE EMBODIMENTS

In order to make the technical problems to be solved, technical solutions and advantages of the present invention clearer, the present invention will be described in detail below with reference to the drawings and specific embodiments.

Figure 1:
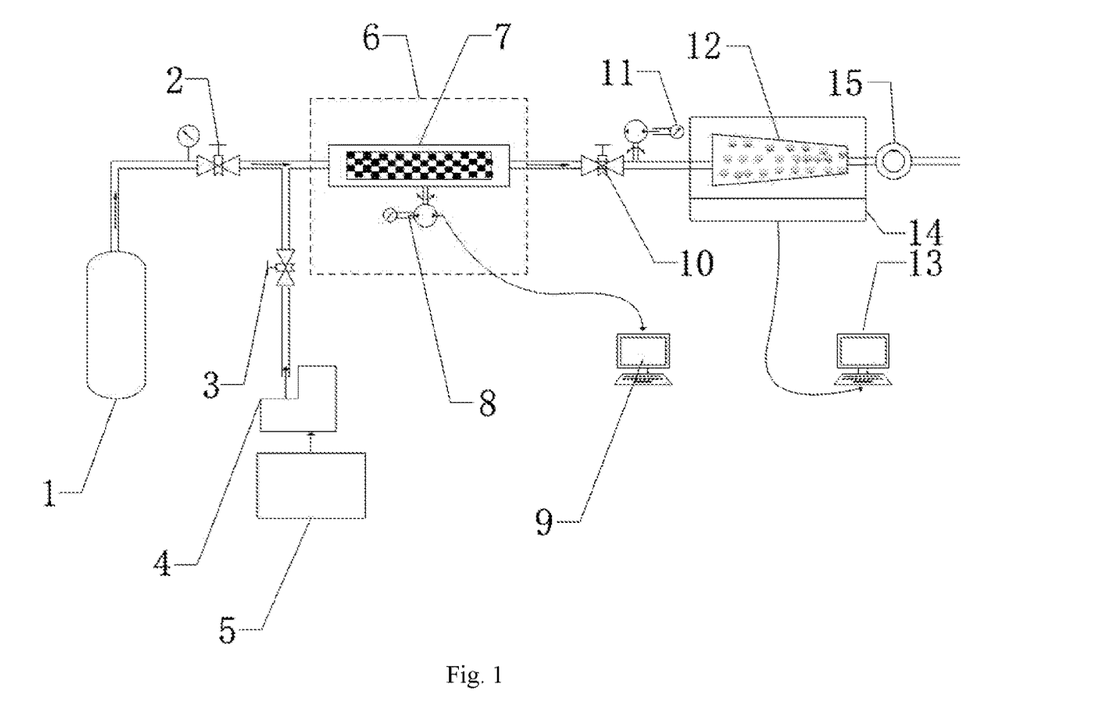
FIG. 1 is a structural schematic diagram of a device for evaluation a gas-water two-phase flow fracture conductivity of a fractured shale according to the present invention.

The present invention provides a device and a method for evaluating a gas-water two-phase flow fracture conductivity of a fractured shale. As shown in FIG. 1, the device includes an injection system, a seepage system, a data collecting and processing system, and the three-axis shale core holder 7.

The injection system includes the gas source 1, the gas inlet pressure regulating valve 2, the water inlet pressure regulating valve 3, the constant-speed constant-pressure pump 4 and the aqueous fracturing fluid 5. The injection system includes the gas source 1 which is generally a nitrogen bottle simulating a natural gas, and the gas inlet pressure regulating valve regulating the pressure in a gas injection stage, and the constant-speed constant-pressure pump 4 for injecting the aqueous fracturing fluid 5 into the seepage system in a water injection stage, so as to realize an alternate driving mode of a constant flow rate and a constant pressure, and the corresponding data analysis is completed.

The seepage system, subjected to two stages including a water injection stage and a gas flooding stage, includes the first back pressure pump 8, the back pressure valve 10, the second back pressure pump 11 and the drying device 12. In the seepage stage, the three-axis shale core holder 7 is placed in the calorstat 6, and the first back pressure pump 8 is set.

In the water injection stage, the seepage system includes the aqueous fracturing fluid 5, the constant-speed constant-pressure pump 4, the water inlet pressure regulating valve 3, the second back pressure pump 11, the back pressure valve 10, and the flow meter 15. The second back pressure pump 11 is connected to the back pressure valve 10, and the back pressure valve 10 is provided between the gas outlet of the shale core holder model and the flow meter 15. The second back pressure pump 11 pumps a liquid, e.g. water, into the rubber pad cavity of the back pressure valve 10, and acts on the gas passing through the back pressure valve 10 through the rubber pad.

In the water injection stage, the aqueous fracturing fluid 5 of the injection system is injected into the three-axis shale core holder 7 at a constant speed or a constant pressure. The aqueous fracturing fluid subjected to the shale core seepage passes through the gas outlet of the shale core holder model, and flows into the flow meter 15 through the back pressure valve 10 for a flow measurement of the aqueous fracturing fluid subjected to the shale core seepage; when the flow rate of the outlet water remains unchanged within 24 hours, the water injection is ended, and the flow rate in the process is recorded to calculate the permeability.

In the gas flooding stage, the seepage system includes the gas source 1 of the nitrogen bottle, the gas inlet pressure regulating valve 2, the second back pressure pump 11, the back pressure valve 10, the drying device 12 on the analytical balance 14, and the flow meter 15. The drying device 12 is configured to collect the water discharged in the gas flooding stage, and then the mass of the water is obtained by the analytical balance 14 and the analytical balance data module 13.

In the gas flooding stage, the gas source 1 of the injection system enters the three-axis shale core holder 7 through the gas inlet pressure regulating valve 2, the aqueous fracturing fluid subjected to the shale core seepage passes through the gas outlet of the shale core holder model, and flows into the flow meter 15 after flowing into the drying device 12 through the back pressure valve 10. When the flow meter 15 detects that the flow rate remains unchanged within 24 hours, the gas injection is ended. The data of the drying device 12 is obtained by the analytical balance data module 13.

The data collecting and processing system includes the strain gauge detector 9, the analytical balance data module 13, the analytical balance 14 and the flow meter 15. The stress patch of the strain gauge detector 9 is provided on the first back pressure pump 8 to record the change of the confining pressure pump during the water influx process, which can be used to describe the impact of the water influx on the confining pressure of the shale core. The flow meter 15 is configured to measure the flow rate of the gas subjected to the shale core seepage through the back pressure valve 10 into the flow meter 15. The analytical balance data module 13 is used to measure the mass of the water absorbed by the drying device, wherein the water is discharged from the shale core in the gas flooding stage.

The three-axis shale core holder 7 is provided in the calorstat 6. The three-axis shale core holder 7 is composed of an inner cavity surrounded by a holder model and an outer cavity outside the holder model, the inner cavity is provided with a shale core, and the outer cavity is a confining pressure cavity. The holder model is preferably in a form of a rubber casing. The holder model is provided with a gas inlet and a gas outlet.

The gas source 1 is connected to the three-axis shale core holder 7 through a pipeline, and the gas inlet pressure regulating valve 2 is provided between the gas source 1 and the three-axis shale core holder 7. The aqueous fracturing fluid 5 is connected to the constant-speed constant-pressure pump 4, and the constant-speed constant-pressure pump 4 is connected to the three-axis shale core holder 7 through a pipeline. The water inlet pressure regulating valve 3 is provided between the constant-speed constant-pressure pump 4 and the three-axis shale core holder 7. The three-axis shale core holder 7 is connected to the first back pressure pump 8, and the first back pressure pump 8 is connected to the strain gauge detector 9. When the seepage system is in the water injection stage, the three-axis shale core holder 7 is connected to the flow meter 15, and when the seepage system is in the gas flooding stage, the gas outlet of the three-axis shale core holder 7 is connected to the drying device 12. The back pressure valve 10 and the second back pressure pump 11 are provided on the pipeline between the three-axis shale core holder 7 and the drying device 12. The drying device 12 is provided on the analytical balance 14, the other end of the drying device 12 is connected to the flow meter 15, and the analytical balance 14 is connected to the analytical balance data module 13.

The following description will be made in combination with specific embodiments.

Embodiment 1

A test sample of a shale is cut and processed into a cylinder, the cylinder is fractured, and the test sample of the shale is dried after cutting and processing at 102° C. for 24 hours.

A cross-sectional area and a length of the test sample of the shale is obtained after drying, a side of a cylindrical shale core after drying is coated with an epoxy silica gel, and after drying, the test sample is weighed for subsequent use.

A temperature of the calorstat 6 is set to 45° C.

The test sample is placed in the shale core holder 7. In order to investigate the hydration reaction after the water influx to the shale fracture, the first back pressure pump 8 is set at a low confining pressure of 2 MPa. In order to prevent the factor of shale creep, the experiment is started after the confining pressure is stable for 12 hours, and the initial permeability is measured by the gas injection seepage system.

Figure 2:
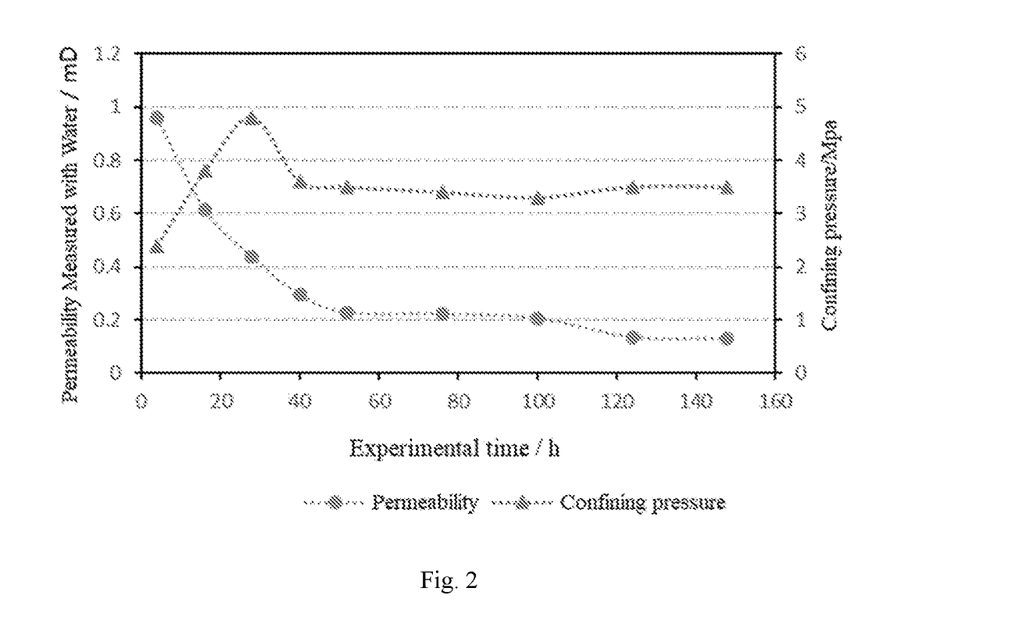
FIG. 2 is a diagram showing a change curve of a permeability measured with water over time and a change curve of a confining pressure over time according to embodiment 1 of the present invention.

Water Injection Stage:

The valve 2 is closed, the constant-speed constant-pressure pump 4 is set as constant pressure injection with an injection pressure of 0.8 MPa. The valve 3 is opened, the aqueous fracturing fluid subjected to the shale core seepage passes through the gas outlet of the shale core holder model, and flows into the flow meter 15 through the back pressure valve 10 for a flow measurement of the aqueous fracturing fluid subjected to the shale core seepage; when the flow rate of the outlet water remains unchanged within 24 hours, and the water injection is ended. The flow rate in this process is recorded, the permeability is obtained by Darcy's law, and the curve of change in the permeability measured with water over time is plotted. The change of the confining pressure in this process is recorded by the strain gauge detector, and the curve of change in the confining pressure under the action of shale hydration swelling during the water influx into the shale core fracture over time is obtained, as shown in FIG. 2.

Embodiment 2

Step 1: Preparation Stage of the Experiment:

A test sample of a shale is cut and processed into a cylinder, the cylinder is fractured, and the test sample of the shale is dried after cutting and processing at 102° C. for 24 hours.

A cross-sectional area and a length of the test sample of the shale is obtained after drying, a side of a cylindrical shale core after drying is coated with an epoxy silica gel, and after drying, the test sample is weighed for subsequent use.

A temperature of the calorstat 6 is set to 45° C.

The test sample of the shale is placed in the shale core holder 7. The back pressure valve 10 is set as 2 MPa, and the first back pressure pump 8 is set at a low confining pressure of 12 MPa. In order to prevent the factor of shale creep, the experiment is started after the confining pressure is stable for 12 hours, and the initial permeability is measured by the gas injection seepage system.

Step 2: Water Injection Stage:

The valve 2 is closed, the constant-speed constant-pressure pump 4 is set as constant pressure injection with an injection pressure of 7 MPa. The valve 3 is opened, the aqueous fracturing fluid subjected to the shale core seepage passes through the gas outlet of the shale core holder model, and flows into the flow meter 15 through the back pressure valve 10 for a flow measurement of the aqueous fracturing fluid subjected to the shale core seepage; when the flow rate of the outlet water remains unchanged within 24 hours, and the water injection is ended. The flow rate in this process is recorded, the permeability is obtained by Darcy's law, and the curve of change in the permeability measured with water over time is plotted. Meanwhile, a discharged liquid from the flow meter is collected, and a discharging amount of the aqueous fracturing fluid is subtracted from an injection amount of the aqueous fracturing fluid to obtain a retention amount of the water in the shale core.

Step 3: Gas Flooding Stage:

The valve 3 is closed, and the drying device 12, the analytical balance 14, and the analytical balance data module 13 are installed. The gas inlet pressure regulating valve 2 is opened and adjusted, the inlet pressure is set to be 3 MPa, and the injection of gas into the three-axis shale core holder is started. The aqueous fracturing fluid subjected to the shale core seepage passes through the gas outlet of the shale core holder model, and flows into the flow meter 15 after flowing into the drying device 12 through the back pressure valve 10. When the flow meter 15 detects that the flow rate remains unchanged within 24 hours, the gas injection is ended. The flow rate in this process is recorded, the permeability is obtained by Darcy's law, and the curve of change in the permeability measured with gas over time is plotted.

Figure 3:
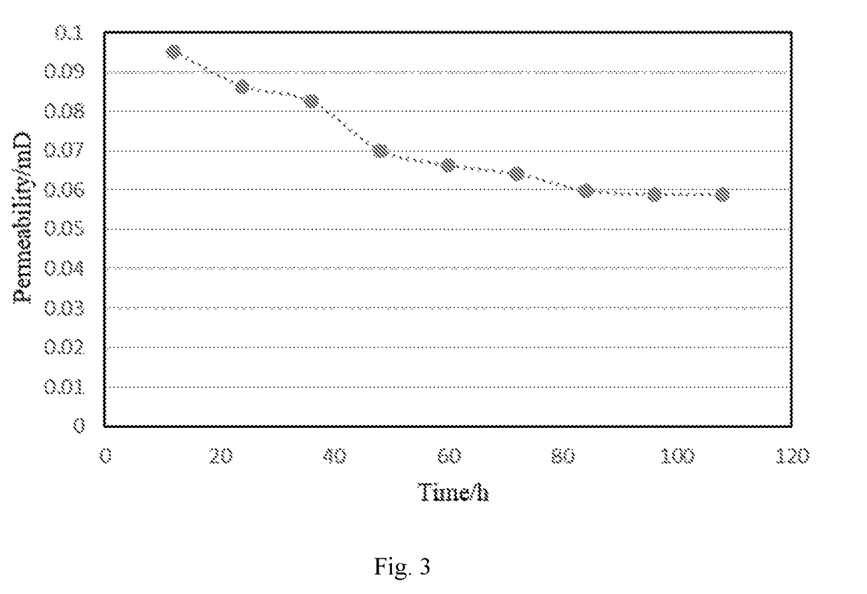
FIG. 3 is a diagram showing a first change of a permeability measured with water over time according to an embodiment of the present invention.
Figure 4:
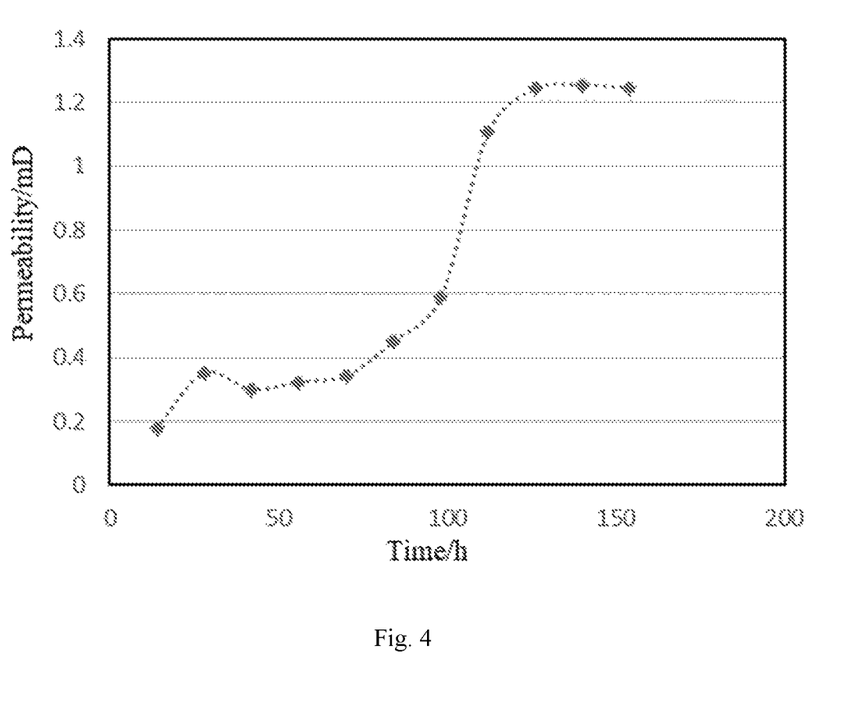
FIG. 4 is a diagram showing a second change of a permeability measured with water over time according to an embodiment of the present invention.

Step 4: Data Processing:

The data processing is performed after the experimental device is closed, and the curve of change in the permeability measured with water over time and the curve of change in the permeability measured with gas over time are plotted to study the permeability change, referring to FIGS. 3-4.

Figure 5:
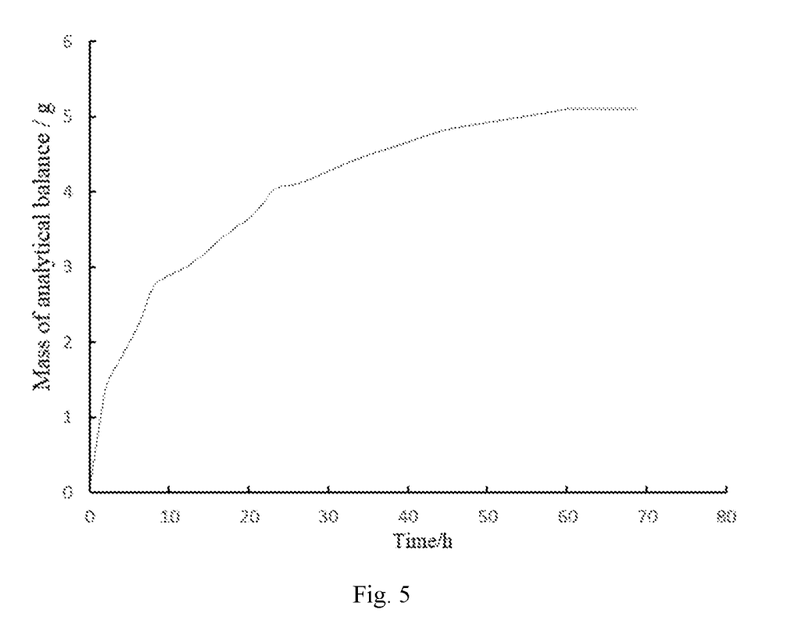
FIG. 5 is a diagram showing a change of a mass measured by an analytical balance over time in a gas flooding stage according to an embodiment of the present invention.

The analytical balance data module is used to obtain a mass of the water discharged from the shale core in the gas flooding stage, referring to FIG. 5. The mass of the water obtained by the analytical balance data module is subtracted from the retention amount of the water in the shale core to obtain an amount of the irreducible water in the shale fracture after the influx of the aqueous fracturing fluid.

Figure 6:
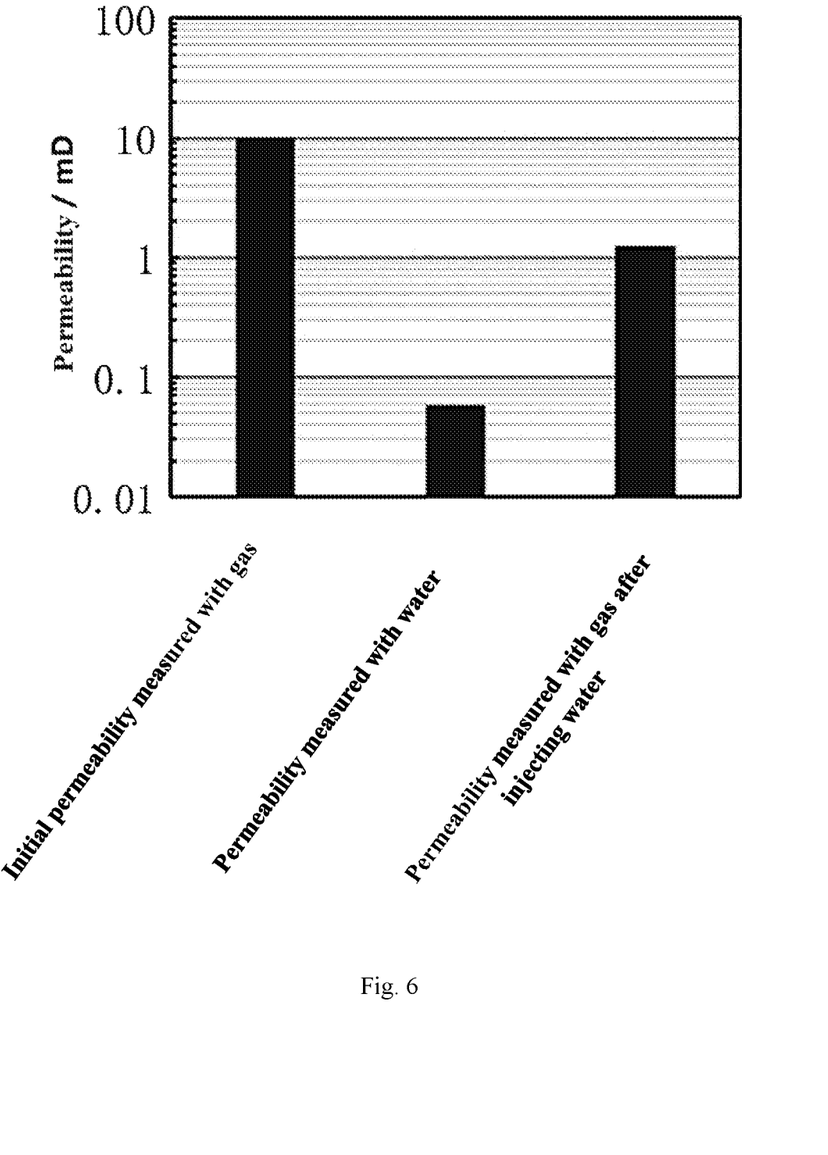
FIG. 6 is a diagram showing a permeability damage situation according to an embodiment of the present invention.

As shown in FIG. 6, after the gas flooding stage is stabilized, the permeability finally obtained is K, an initial permeability is $K_0$, and then a permeability damage rate f can be obtained by the following formula:

$$f = \frac{K - K_0}{K} \times 100\%.$$

The above description shows preferred embodiments of the present invention. It should be noted that various modifications and improvements may be made by those skilled in the art without departing from the principles of the present invention, and such modifications and improvements should also be considered as falling within the scope of the present invention.

What is claimed is:

1. A device for evaluating a gas-water two-phase flow fracture conductivity of a fractured shale, comprising: an injection system, a seepage system, a data collecting and processing system, and a three-axis shale core holder; wherein, the injection system comprises a gas source, a gas inlet pressure regulating valve, a water inlet pressure regulating valve, a constant-speed constant-pressure pump and an aqueous fracturing fluid; the seepage system is subjected to two stages including a water injection stage and a gas flooding stage, the seepage system comprises a first back pressure pump, a back pressure valve, a second back pressure pump and a drying device; the data collecting and processing system comprises a strain gauge detector, an analytical balance data module, an analytical balance, and a flow meter; the three-axis shale core holder is provided in a calorstat, the gas source is connected to the three-axis shale core holder through a pipeline, the gas inlet pressure regulating valve is provided between the gas source and the three-axis shale core holder, the aqueous fracturing fluid is connected to the constant-speed constant-pressure pump, the constant-speed constant-pressure pump is connected to the three-axis shale core holder through a pipeline, and the water inlet pressure regulating valve is provided between the constant-speed constant-pressure pump and the three-axis shale core holder; the three-axis shale core holder is connected to the first back pressure pump, and the first back pressure pump is connected to the strain gauge detector; when the seepage system is in the water injection stage, the three-axis shale core holder is connected to the flow meter, and when the seepage system is in the gas flooding stage, a gas outlet of the three-axis shale core holder is connected to the drying device; the back pressure valve and the second back pressure pump are provided on the pipeline between the three-axis shale core holder and the drying device; the drying device is provided on the analytical balance, the other end of the drying device is connected to the flow meter, and the analytical balance is connected to the analytical balance data module.

2. The device for evaluating the gas-water two-phase flow fracture conductivity of the fractured shale of claim 1, wherein, the three-axis shale core holder is composed of an inner cavity surrounded by a holder model and an outer cavity outside the holder model, the inner cavity is provided with a shale core, and the outer cavity is a confining pressure cavity; the holder model is in a form of a rubber casing; and the holder model is provided with a gas inlet and a gas outlet.

3. The device for evaluating the gas-water two-phase flow fracture conductivity of the fractured shale of claim 1, wherein, the gas source is a nitrogen bottle.

4. The device for evaluating the gas-water two-phase flow fracture conductivity of the fractured shale of claim 1, wherein, a value of a confining pressure in the three-axis shale core holder is set to be at least 1 MPa higher than an inlet pressure of the three-axis shale core holder by the seepage system.

5. The device for evaluating the gas-water two-phase flow fracture conductivity of the fractured shale of claim 1, wherein, in the water injection stage of the seepage system, the aqueous fracturing fluid is injected into the three-axis shale core holder at a constant speed or constant pressure; the aqueous fracturing fluid subjected to a shale core seepage passes through the gas outlet of the three-axis shale core holder, flows into the flow meter through the back pressure valve, and a flow rate of the aqueous fracturing fluid subjected to the shale core seepage is measured by the flow meter.

6. The device for evaluating the gas-water two-phase flow fracture conductivity of the fractured shale of claim 1, wherein, in the gas flooding stage of the seepage system, the gas source enters the three-axis shale core holder through the gas inlet pressure regulating valve; the aqueous fracturing fluid subjected to the shale core seepage passes through the gas outlet of the three-axis shale core holder, flows into the drying device through the back pressure valve, and then flows into the flow meter; and a mass of the water inside the shale core is obtained by the analytical balance data module according to data of the drying device.

7. A method of using the device for evaluating the gas-water two-phase flow fracture conductivity of the fractured shale of claim 1, comprising the following steps:

(1) preparation stage of an experiment:
cutting and processing a test sample of a shale into a cylinder, fracturing the cylinder, drying the test sample of the shale after cutting and processing at 102° C. for 24 hours;
obtaining a cross-sectional area and a length of the test sample of the shale after drying, coating a side of a cylindrical shale core of the test sample after drying with an epoxy silica gel, and after drying, weighing the test sample;
setting a temperature of the calorstat to 45° C.; and
putting the test sample into the three-axis shale core holder; setting the back pressure valve, adding a confining pressure to the first back pressure pump, after the confining pressure is stable for 12 hours, starting the experiment, and measuring an initial permeability by a gas injection seepage system;

(2) water injection stage:
closing the gas inlet pressure regulating valve, setting the constant-speed constant-pressure pump as a constant pressure injection, setting an injection pressure according to a specific condition of the shale core, opening the water inlet pressure regulating valve, making the aqueous fracturing fluid subjected to the shale core seepage pass through the gas outlet of the three-axis shale core holder, and flow into the flow meter through the back pressure valve, and measuring the flow rate of the aqueous fracturing fluid subjected to the shale core seepage by the flow meter; when the flow rate of the outlet water remains unchanged within 24 hours, ending the water injection, recording the flow rate in this process, obtaining a permeability by Darcy's law, and plotting a curve of change in the permeability measured with water over time; collecting a discharged liquid from the flow meter, and subtracting a discharging amount of the aqueous fracturing fluid from an injection amount of the aqueous fracturing fluid to obtain a retention amount of the water in the shale core; (3) gas flooding phase:

closing the water inlet pressure regulating valve, installing the drying device, the analytical balance, and the analytical balance data module; setting an inlet pressure of the gas source according to a specific condition of the shale core, opening and adjusting the gas inlet pressure regulating valve, starting to inject the gas into the three-axis shale core holder, and making the aqueous fracturing fluid subjected to the shale core seepage pass through the gas outlet of the three-axis shale core holder, and flow into the flow meter after flowing into the drying device through the back pressure valve; when the flow meter detects that the flow rate remains unchanged within 24 hours, ending the gas injection, recording the flow rate in this process, obtaining a permeability by Darcy's law, and plotting a curve of change in the permeability measured with gas over time; and (4) data processing:
performing the data processing after closing the experimental device, and plotting the change curve of the permeability measured with water over time and the curve of change in the permeability measured with gas over time to study a permeability change;
using the analytical balance data module to obtain a mass of the water discharged from the shale core in the gas flooding stage in the drying device, subtracting the mass of the water the obtained by the analytical balance data module from the retention amount of the water in the shale core to obtain an amount of irreducible water in the shale fracture after the influx of the aqueous fracturing fluid; and
after the gas flooding stage is stable, obtaining the permeability K, an initial permeability is $K_0$, and then a permeability damage rate $f$ is obtained by the following formula:

$$f = \frac{K - K_0}{K} \times 100\%.$$

* * * * *